United States Patent [19]

Weidman et al.

[11] 4,261,040
[45] Apr. 7, 1981

[54] METHOD AND APPARATUS FOR THE ANALYSIS OF SCANNED DATA

[75] Inventors: Peter C. Weidman; Wayne E. Woodmansee, both of Seattle, Wash.

[73] Assignee: The Boeing Company M/S 7E-25, Seattle, Wash.

[21] Appl. No.: 44,721

[22] Filed: Jun. 1, 1979

[51] Int. Cl.³ .................. H04N 1/22; H04N 5/14
[52] U.S. Cl. .................. 364/554; 364/515; 358/166
[58] Field of Search ............... 364/554, 413, 514, 515; 358/160, 166

[56] References Cited

U.S. PATENT DOCUMENTS

| | | | |
|---|---|---|---|
| 3,637,997 | 1/1972 | Petersen | 235/92 N |
| 3,706,851 | 12/1972 | Froehlich | 358/96 |
| 3,787,666 | 1/1974 | Schumann et al. | 364/521 X |
| 3,856,985 | 12/1974 | Yokoi et al. | 358/96 X |
| 3,903,357 | 9/1975 | Woolfson et al. | 178/6.8 |
| 3,925,606 | 12/1975 | Wood | 178/6.8 |
| 3,969,571 | 7/1976 | Fenyo | 358/166 |
| 3,982,425 | 9/1976 | McLain | 364/506 X |
| 3,983,320 | 9/1976 | Ketcham et al. | 358/166 |
| 3,987,243 | 10/1976 | Schwartz | 358/166 X |
| 4,041,286 | 8/1977 | Sanford | 358/139 X |
| 4,068,310 | 1/1978 | Friauf | 364/521 |
| 4,075,658 | 2/1978 | de Cosnac et al. | 358/96 |
| 4,079,417 | 3/1978 | Scudder | 358/111 |
| 4,099,240 | 7/1978 | Rode et al. | 364/571 |
| 4,115,804 | 9/1978 | Morton et al. | 364/515 X |
| 4,124,871 | 11/1978 | Morrin | 358/287 |
| 4,127,873 | 11/1978 | Katagi | 358/166 |
| 4,143,401 | 3/1979 | Coviello | 364/515 X |
| 4,149,248 | 4/1979 | Pavkovich | 364/515 X |
| 4,159,522 | 6/1979 | Zanoni | 364/515 |

Primary Examiner—Edward J. Wise
Attorney, Agent, or Firm—James P. Hamley; Bernard A. Donahue

[57] ABSTRACT

A material under test is scanned by transmit and receive ultrasonic transducers, thus generating data representative of the structural integrity of the material at precise locations thereof. The data is stored in memory for recall to excite a graphics display of the material. A user may define any boundary shape within the display and thereby cause a computer to recall and statistically process only those data points within the boundary.

9 Claims, 5 Drawing Figures

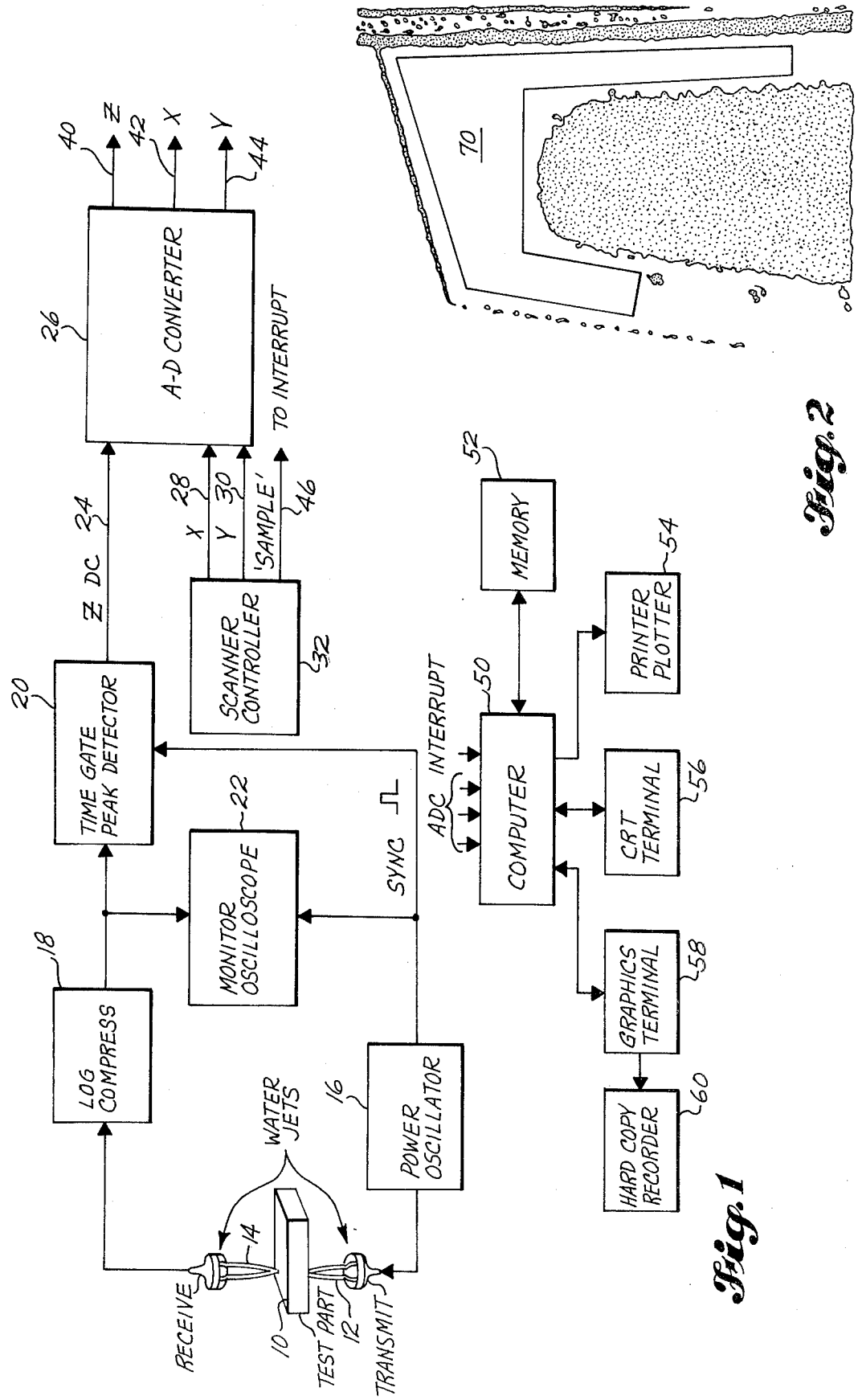

4,261,040

METHOD AND APPARATUS FOR THE ANALYSIS OF SCANNED DATA

BACKGROUND OF THE INVENTION

The present invention pertains to the data processing art and, more particularly, to a method and apparatus for the selective analysis of scanned data.

Numerous systems are known to the prior art which provide a means to analyze scanned data. One such prior art system which particularly relates to the instant invention pertains to nondestructive testing of materials. Here, a transducer scans the material under test in a raster pattern to insure coverage of the area of interest. The detected output of the transducer is then used to drive a two level facsimile recorder. A reference level is set in the recorder. For transducer outputs above and below this level corresponding light and dark areas are formed on the recorder. If, on a given scan, the programmed reference level does not yield the desired material information, a new level is entered and the scan is run again. Thus, for a complete profile of the material several scans must be run.

Further, once a scan is run it is often desirable to do a statistical analysis on selected areas of the material scan. In the prior art now and heretofore, techniques have been developed for sectioning off regularly shaped, generally square, sections of a scan in selecting the data points therein. In many applications, it is desirable to be able to select any given area of the scan for statistical analysis of the data points contained therein.

SUMMARY OF THE INVENTION

It is an object of this invention, therefore, to provide apparatus for storing the results of a material scan and accessing selective ones of the data points for statistical analysis.

It is a further object of the invention to provide apparatus for the testing of a material which includes a means for utilizing the results of a single scan to display various characteristics of the material.

It is an additional object of the invention to provide a method for the display and selective statistical analysis of data points contained within a defined area of a display.

Briefly, according to the invention, the apparatus which tests the material by the use of a scanning transducer, which transducer produces a sequence of output signals X, Y and Z with the signals X and Y defining a structure location and the signal Z being representative of a structural paramater at the X, Y location is characterized by improvements including memory which stores the X, Y, and Z signals. An accessing means accesses selective ones of the X, Y and Z signals representative of a desired section of the material. Processing means performs a predetermined statistical analysis on the selected signals thereby determining a characteristic of the material section.

Further, the apparatus may be provided with a comparator which compares each of the Z signals with a selectable reference level. A provided display produces a display of each of the Z signals, in its relative location as determined by the corresponding X and Y signals, having a predetermined relationship to the reference signal.

The method for the display and selective statistical analysis of a series of data points, wherein each data point is represented by unique position signals X and Y and a magnitude at that position represented by a signal Z, includes the first step of storing each data point X, Y and Z signal in an array. The stored data points are plotted on a graphic display such that the magnitude of the display of each data point corresponds to the Z signal and the relative position of the display of each data point corresponds to the signals X and Y. Thus, a user controlled boundary on the display is generated. Those data points contained within the selected boundary are selected, with a statistical analysis being performed thereon.

BRIEF DESCRIPTION OF THE DRAWINGS

FIG. 1 is an overall block diagram of the preferred embodiment of the nondestructive testing system according to the invention;

FIG. 2 is representative of a sample display provided by the apparatus of FIG. 1;

DETAILED DESCRIPTION OF THE PREFERRED EMBODIMENT OF THE INVENTION

Figure 3A:
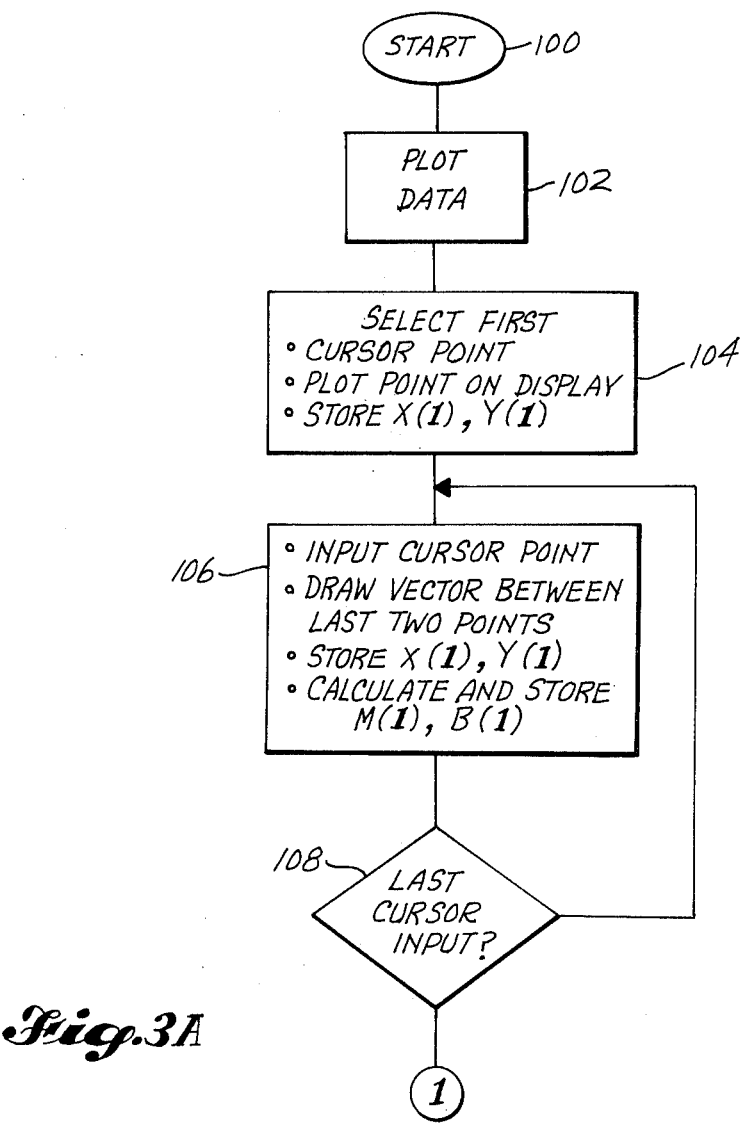
FIGS. 3A and 3B are flow diagrams illustrating the logic operations performed by the computer of FIG. 1.

FIG. 1 is a block diagram of an ultrasonic through transmission material testing system. Here, a portion of the material under test 10 is located between a transmit transducer 12 and a receive transducer 14. Water columns on both sides of the material 10 couple ultrasonic bursts, generated by power oscillator 16, therethrough. The amplitude of the pressure pulse transmitted through the material 10 is monitored by the receive transducer 14 and converted to corresponding analog electrical signals. Means, not shown, causes the transmit 12 and receive 14 transducers to scan the material in unison. Such ultrasonic, scanning transducers are readily commercially available.

The analog signals from the receive transducer 14 are compressed in the log compressor 18, thereby reducing the overall dynamic range of the detected signals for easier signal processing, and applied to the input of a time gate peak detector 20. The power oscillator 16 provides a synchronization, or "sync" signal at an output which is applied to the time gate peak detector 20. The function of time gate peak detector 20 is to output the signal supplied by the log compressor 18 after a selectable delay following the sync pulse to enable the ultrasonic pulse to travel through the test object and coupling media. Thus, the output of time gate peak detector 20 is the precise through transmission response of the material corresponding to the maximum received signal detected within the gated interval.

A monitor oscilloscope 22, which is triggered off the power oscillator sync pulse, monitors the output of log compression amplifier 18 to display to the operator the instantaneous response of the system.

The DC analog output from time gate peak detector 20 is applied on a first line 24 to an input of an analog to digital converter 26. Also applied to input lines 28–30 of analog to digital converter 26 are the position outputs from a scanner controller 32. Scanner controller 32 includes the apparatus which controls and drives the scanning of the transmit and receive transducers 12, 14. The instantaneous position of the transducers is represented by an analog X coordinate signal on line 28 and an analog Y coordinate signal on line 30. Analog to digital converter 26 operates in the conventional manner to convert the signals on its input lines 24, 28 and 30 to corresponding digital signals at its output lines 40, 42 and 44, respectively. A digital signal representative of the DC amplitude on line 24 is designated as a Z coordinate whereas the X and Y inputs on lines 28, 30 retain their identity.

In an alternative arrangement, the X and Y position signals, rather than being derived from digitized analog signals, may be generated from the sampling pulses occurring at regular Y axis increments together with a discrete direction voltage which determines the manner in which data is output to the display. This reduces the data storage requirement.

The scanner controller 32 also provides an output line 46 which is a sample interrupt signal.

The interrupt signal controls the sampling of the test data by the analog to digital connecter. As the transducers scan the test object, the scan controller generates interrupt pulses at regular intervals, typically 1 per millimeter, to sample in the Y direction. The X axis increment is typically fixed in either 1.5 mm or 6.0 mm.

The digital X, Y and Z signals, as well as the interrupt signal are fed to the inputs of a computer 50. While the precise operation of the computer 50 is described more fully with respect to FIGS. 3A, 3B and 4, for the purposes of FIG. 1 the computer 50 loads the data points into a memory 52. Memory 52 may be comprised of any conventional memory means such as tape, disc or electronic memory.

Once all of the data points have been loaded into memory 52, the computer 50, responding to its internal programing, outputs the data to a conventional printer plotter 54 and a graphics terminal 58 which in turn drives a hard copy recorder 60.

System control is provided via a standard CRT terminal 56. FIG. 2 is representative of a sample display produced by the system of FIG. 1. The display is representative of the part under test in that the relative brightness of each data point is representative of the amplitude of the Z signal at the relative position on the sample as determined by the X, Y coordinate signals. Thus, for example, the computer compares the Z level of each data point with a programable reference level. If the Z level is less than the reference level this may be displayed as either a light or dark area dependent upon programing. Correspondingly, if the Z value is greater than the reference this may be displayed as a dark or light region. By changing the programable reference level the computer 50 can produce different displays of the material showing its various characteristics. This eliminates the repetitive scans required in the prior art.

Also, an operator, via use of the graphics terminal 58, can define a boundary area, indicated generally at 70, from which data points are to be selected for statistical processing. The manner in which this is done is more fully understood with reference to FIGS. 3A, 3B and 4.

Figure 3B:
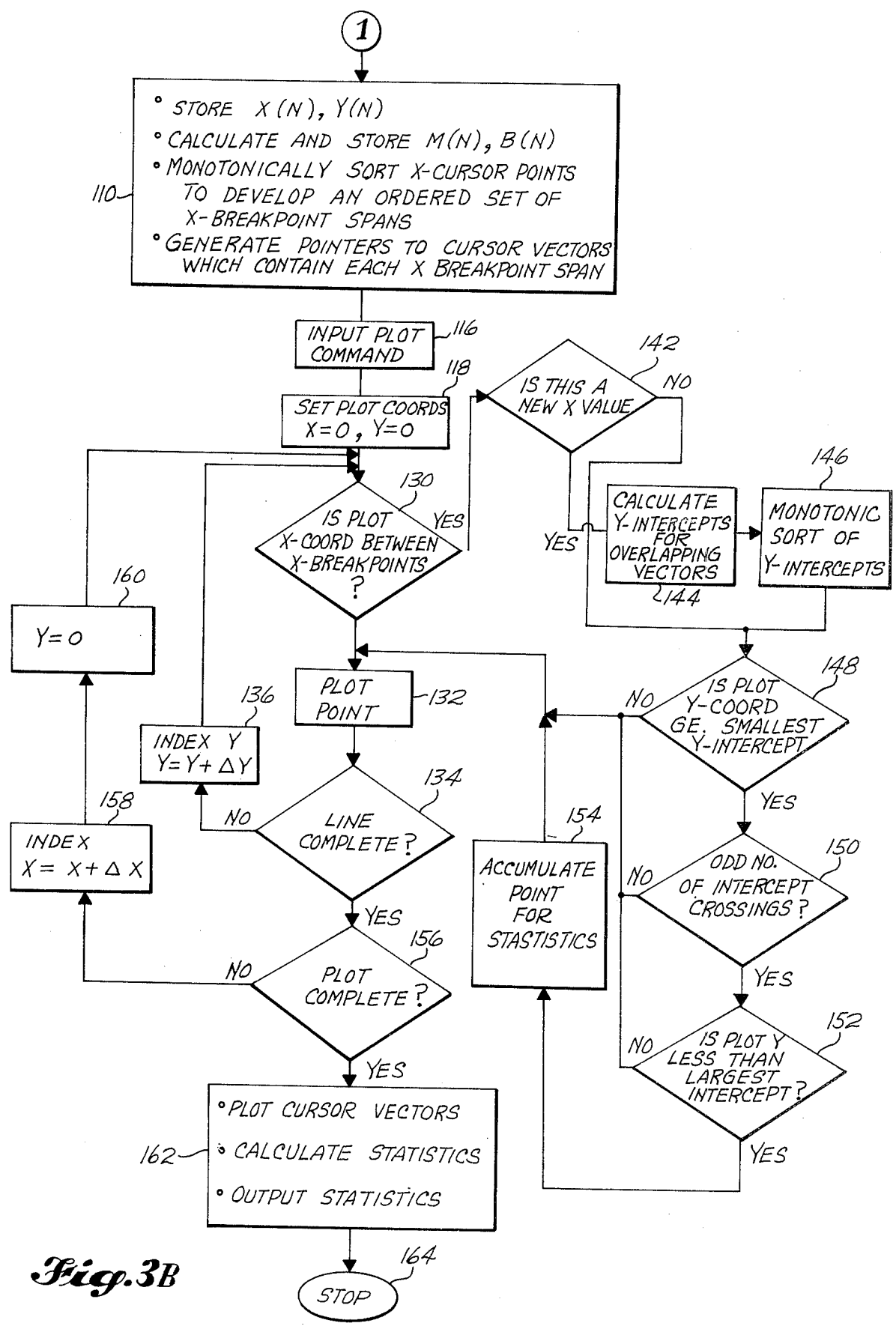
Figure 4:
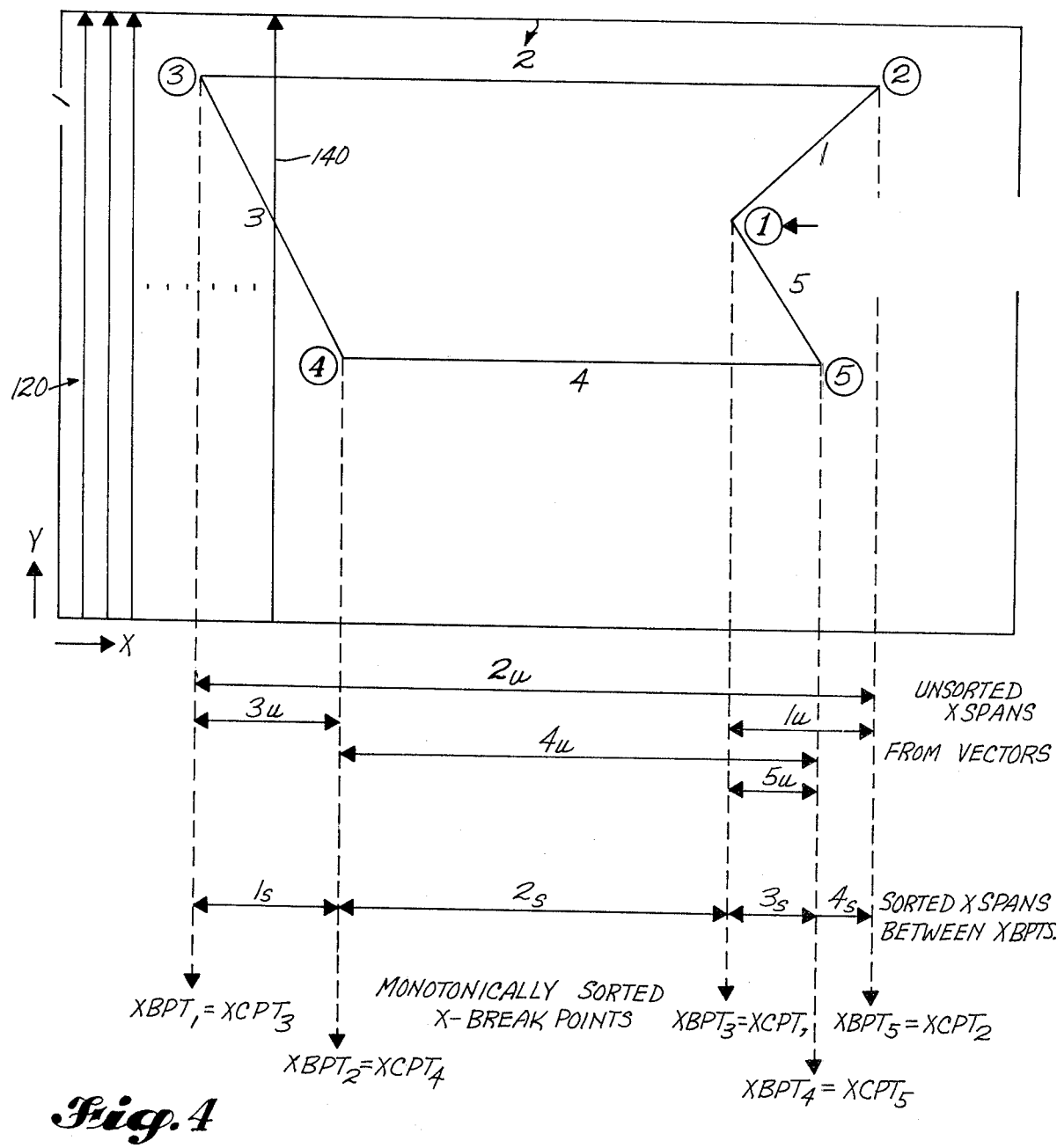
FIG. 4 is a graph illustrating pictorially the operations performed by the computer shown in FIG. 1.

FIGS. 3A and 3B are flow diagrams illustrating the sequences performed by the computer 50 of FIG. 1 to create the data display, allow a user to define any boundary within the display and perform statistical analysis only on data points within that boundary. FIG. 4 pictorially depicts the process which the computer performs.

Referring to FIG. 3A, the computer begins its operation at the start 100. The X, Y and Z signals corresponding to each data point are recalled from memory 52 (FIG. 1) and plotted on the graphics display, as indicated by block 102. Upon viewing the display, a user may define any shaped boundary for statistical analysis. This begins, as indicated in block 104 by selecting a first cursor point on the boundary. Referring to FIG. 4, the first cursor point is indicated by ①. The X, Y coordinates of this point are stored in memory and point ① is plotted on the display. The process continues by selecting the next cursor point, here point ② in FIG. 4, as indicated in block 106. A vector is then drawn between points ① and ②. The X and Y coordinates of the next point are stored and the computer calulates the slope, and Y intercept of the vector between points ① and ②.

Block 108 then poses the question as to whether this is the last cursor point. If the answer is no the system returns to inputting the next cursor point, and continues as per block 106. In the example shown in FIG. 4, a total of 5 cursor points are utilized. It should be understood, however, that any number of cursor points could be provided.

Once the last cursor point is entered, the computer continues in accordance with the flow diagram of FIG. 3B. Here, as indicated by block 110, the last cursor point, i.e. point ⑤ in FIG. 4, has its X and Y coordinates stored and a vector is drawn between the last point and the first point ①. The slope and Y intercept M(N), B(N), respectively, are calculated and stored for this vector.

The computer then monotonically sorts the X cursor points to develope an increasing list of sorted X break points. Thus, referring to FIG. 4, $X(③) < X(④)$ $X(①) < X(⑤) < X(②)$.

Next, the vectors are examined to determine the set of their X spans which fully overlap each of the spans of the ordered, or sorted X spans. In the example shown in FIG. 4, the X span of the vectors labeled $2_u$ and $3_u$ overlap the sorted X span $1_s$; the vectors labeled $2_u$ and $4_u$ overlap sorted X span $2_s$; the vectors labeled $1_u$, $2_u$, $4_u$ and $5_u$ overlap sorted X span $3_s$; and vectors labeled $1_u$ and $2_u$ overlap sorted X span $4_s$.

Plotting of the stored sample points originates at the lower left corner of the display and takes place from bottom to top, as indicated by blocks 116 and 118 of FIG. 3B and the arrows, indicated generally by reference numeral 120 in FIG. 4. Following logic flow diagram 3B, at block 130 the X coordinate of the plot is tested for being between successive break points. If it is not, the point is plotted, at block 132, and the test is made at block 134, to determine whether or not the vertical line is complete, i.e. whether or not the Y coordinate of the plot exceeds the highest allowed Y coordinate of the display. If the line is not complete, the system increments the Y value by a value Δ Y, as indicated at block 136. The system then reverts to block 130 to determine whether or not the X coordinate of the plot is between X break points.

This process continues until, as shown at line 140 in FIG. 4, the X coordinate of the plot is in fact between X break points. Now, at block 142, a determination is made as to whether the X value is a new X value, i.e. whether the X value has been incremented from its previous value at the time of the test at block 142. If it is, the system increments to block 144 and calculates the Y intercepts of the plot with overlapping vectors between the X break points. As Block 146 a monotonic sort is done of the Y intercepts to determine in which order the plot will intercept vectors. Thus, as in FIG. 4, the plot line 140 will intercept vector 3 prior to intercepting vector 2.

After completing the monotonic sort of Y intercepts, the system, in block 148, determines whether or not the plotted Y coordinate is greater than or equal to the smallest Y intercept. If no, the system reverts to plot point block 132. If yes, a test is done, at block 150, to determine whether or not the plot has passed an odd number of intercept crossings. If no, the system reverts to plot point block 132 whereas if yes a test is made at block 152, to determine whether or not the plotted Y coordinate is less than the largest Y intercept. If no, the system reverts to plot point block 132 whereas if the plot is less than the largest Y intercept the point is accumulated for statistics at block 154. The system then returns to the plot point block 132.

In this manner, one complete vertical line scan is made. Once the line is complete, as determined by block 134, the system determines whether or not the entire plot is complete at block 156. If it is not, the X value is indexed by a value Δ X at block 158 and the Y value is reset to zero at block 160, with the sytem returning to block 130 for further iterations.

Finally, once block 156 determines that the plot is complete, it causes the display to plot the cursor vectors, calculate the statistics for the points accumulated by block 154 and output the statistics at block 162. The process being complete, the system then stops, as indicated at block 164.

To summarize the basic method by which data points within any desired boundary are selected, cursor points which define the boundary of the desired area are entered by a user. The system then generates a vector between successive cursor points, and calculates the slope and Y intercept of the vector. When all cursor points have been entered, the system sorts the X spans between cursor break points. A determination is made of which unsorted X spans from the generated vectors are associated with the sorted X spans between cursor break points. The plot, beginning at the origin, generates successive vertical lines. Once it is determined that the X coordinate of the plot is between the sorted X span break points, those unsorted vector X spans which overlap the relevant break points are tested for a Y intercept with the plot. In this way, the system knows which of the vectors is crossed first. If the plot is greater than or equal to the smallest of the vector Y intercepts, and if at that point an odd number of intercept crossings has been made and if the plot is less than the largest vector intercept, then conditions are satisified for the plot being within the defined boundary. Therefore, data points falling on this vertical line and satisfying the above conditions are accumulated for statistics. In this manner, all data points in the scan system within any defined area can be accessed and processed statistically.

While a preferred embodiment of the invention has been described in detail, it should be apparent that many modifications and variations thereto are possible, all of which fall within the true spirit and scope of the invention.

We claim:

1. Apparatus for the testing of a material wherein a scanning transducer means produces a sequence of output signals X, Y and Z, said signals X and Y defining a structure location and said signal Z being representative of a structural parameter at said location, the improvement comprising:

memory means for storing said X, Y and Z signals;
   accessing means for accessing selective ones of said X, Y and Z signals representative of a desired section of said material; and
   processing means for performing a predetermined statistical analysis, corresponding to the type of test being performed, on said selected signals thereby determining a characteristic of said material section.

2. The improvement of claim 1 further including
   comparator means for comparing each of said Z signals with a selectable reference level; and display means for producing a display of each of said Z signals, in its relative location as determined by the corresponding X and Y signals, having a perdetermined relationship to said reference signal.

3. The improvement of claim 2 wherein the accessing means comprises means acting in cooperation with said display means to define any selected area of
   said display and access only those signals contained therein for statistical processing by said processing means.

4. Apparatus for the testing of a material wherein a scanning transducer means produces a sequence of output signals X, Y and Z, said signals X and Y defining a structure location and said signal Z being representative of a structural parameter at said location, the improvement comprising:

memory means for storing said X, Y and Z signals;
   comparator means for comparing each of said stored signals with a selectable reference level; and
   display means for producing a display of each of said Z signals, in its relative location as determined by the corresponding stored X and Y signals, having a predetermined relationship to said reference level.

5. The improvement of claim 4 further comprising:
   accessing means for accessing selective ones of said X, Y and Z signals representative of a desired section of said material; and
   processing means for performing a predetermined statistical analysis on said selected signals thereby determining a characteristic of said material section.

6. The improvement of claim 5 wherein the accessing means comprises means acting in cooperation with said display means to define any selected area of said display and access only those signals contained therein for statistical processing by said processing means.

7. A method for the display and selective statistical analysis of a series of data points, each data point being represented by unique position signals X and Y and a magnitude at said position represented by a signal Z, the method including the steps of:

(a) storing each data point X, Y and Z signal in an array,
   (b) plotting said stored data points on a graphic display such that the magnitude of the display of each data point corresponds to said Z signal and the relative position of the display of each data point corresponds to said signals X and Y;
   (c) generating a user controlled boundary on said display;
   (d) selecting only those data points contained within said selected boundary; and
   (e) performing a predetermined statistical analysis on only those displayed data points within said boundary.

8. The method of claim 7 wherein the step of generating a user controlled boundary comprises the steps of:
   (a) providing a user controlled first cursor boundary point on said display, said point having position coordinates X (1), Y (1);
   (b) storing said coordinates X (1), Y (1);
   (c) providing a user controlled second cursor boundary point on said display, said point having position coordinates X (2), Y (2);
   (d) storing said coordinates X (2), Y (2);
   (e) displaying a vector between said first and second cursor points;
   (f) calculating and storing the slope and intercept of said vector; and
   (g) repeating the steps above for the remaining cursor boundary points including displaying vectors between successive cursor points, and between the last and the first cursor points, and calculating and storing the slope and intercept of each vector.

9. The method of claim 8 wherein the step of selecting only those data points contained within the selected boundary comprises the steps of:
   (a) sorting the X coordinates of the cursor points to form a monotonically increasing value list thereof;
   (b) determining the X span of each of the vectors between successive cursor points;
   (c) determining which of the unsorted vector X spans are associated with successive pairs of the sorted cursor X coordinates;
   (d) scanning the display by incrementing in values of Y from an origin value to the highest Y value allowed at which time the X value is incremented by a predetermined value X and Y is again incremented from its origin value to its highest allowed value, repeating this process until the entire display has been scanned;
   (e) during scanning step (d)
      (i) upon the instantaneous incremented X value exceeding a sorted X coordinate cursor point, those vectors having X spans which overlap said cursor point and its successive cursor points are sorted according to increasing Y intercept values with said incremented scan,
      (ii) upon the scan incrementing in Y value to the first vector intercept, comparing the incremental scanned value with the stored data point value and selecting those data point values equaling the scanned value until the scan increments to the next intercept with a vector;
      (iii) selecting subsequent data points whose coordinates match the instantaneous scan value for scan values which are between odd and even number Y intercepts with the vectors.

* * * * *